United States Patent [19]

Bisera et al.

[11] 4,028,931
[45] June 14, 1977

[54] OSMOTIC PRESSURE SENSING HEAD

[75] Inventors: Jose Bisera, Camarillo; James Howard Carrington, Los Angeles; Max Harry Weil, Beverly Hills, all of Calif.

[73] Assignee: Cardio Pulminary Laboratory Research Foundation, Los Angeles, Calif.

[22] Filed: Feb. 13, 1976

[21] Appl. No.: 657,837

[52] U.S. Cl. .............................................. 73/64.3
[51] Int. Cl.² ..................................... G01N 13/04
[58] Field of Search ................... 73/64.3; 23/230 B

[56] References Cited

UNITED STATES PATENTS 3,628,373  12/1971  Gilbert ........................... 73/64.3

FOREIGN PATENTS OR APPLICATIONS 1,523,472  3/1968  France ............................. 73/64.3

*Primary Examiner*—Richard C. Queisser
*Assistant Examiner*—Joseph W. Roskos
*Attorney, Agent, or Firm*—Lindenberg, Freilich

[57] ABSTRACT

An osmotic sensing head for measuring the osmotic pressure of protein molecules in blood, which is of the type that includes a reference chamber for holding saline solution, a sample chamber for holding blood, an osmotic membrane between the chambers, and a pressure sensor coupled to the reference chamber to measure the pressure therein. The sample chamber has a small volume and is provided with an inlet and outlet so that a storage saline solution can be removed and a blood sample introduced by merely flowing the blood sample in through the inlet while allowing the storage solution to pass out through the outlet. The inlet is directed at the membrane at an angle to help wash away material lying on the membrane. The osmotic membrane is held in slight tension by an elastomeric O-ring which presses the membrane against a conical surface.

3 Claims, 2 Drawing Figures

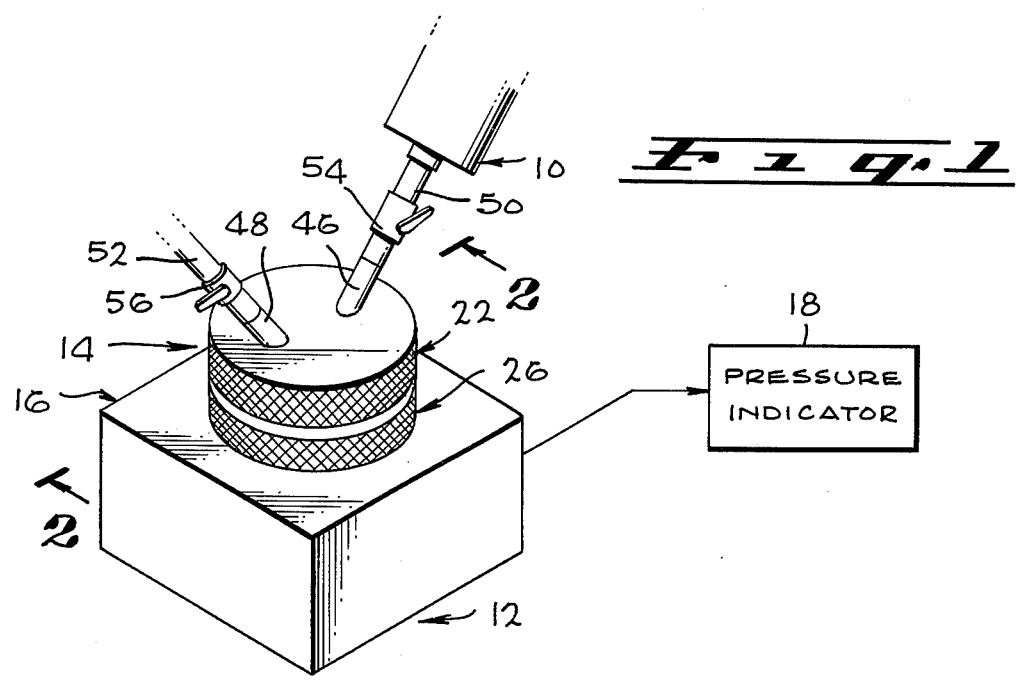
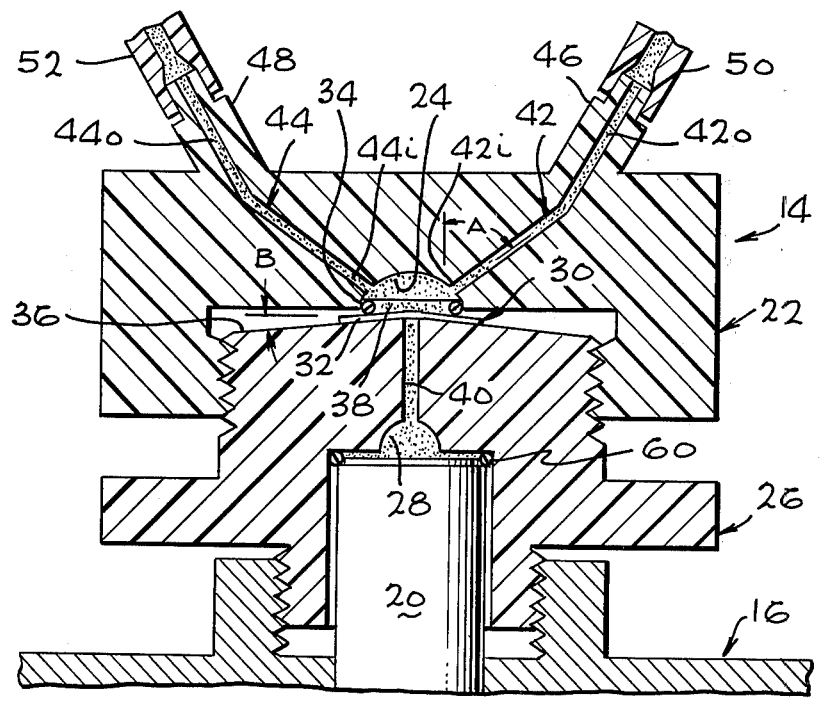

OSMOTIC PRESSURE SENSING HEAD

BACKGROUND OF THE INVENTION

This invention relates to an osmotic pressure sensing head.

The measurement of the osmotic pressure of blood protein molecules in the blood, has become important in the diagnosis of edema, and especially pulmonary edema. It is believed that fluid moving into the alveoli of the lung, which prevents oxygenation of the blood, is due to low levels of blood proteins whose osmotic pressure would normally draw fluid from the alveoli into the capillaries. The plasma colloid osmotic pressure, often referred to as the oncotic pressure, can be measured in a sensing head which includes a reference chamber containing saline solution, a sample chamber for receiving blood plasma, and an osmotic membrane between the chambers which allows saline (NaCl) molecules to pass through while preventing the passage of the much larger protein molecules of the blood. A pressure transducer coupled to the reference chamber measures the pressure resulting from the osmotic pressure of the blood proteins to thereby indicate the concentration of the blood proteins. While such a sensing head enables more rapid determination of the concentration of blood proteins than can be achieved by centrifuging of the proteins and weighing them, the maintenance and operation of such a sensing head is a delicate and often difficult task. The sensing head is normally stored with saline solution on both sides to preserve the membrane. The stored saline solution must be removed and replaced by the blood plasma before each measurement, and the blood plasma must be fully removed after each measurement and the membrane cleaned. Actually, whole blood can be utilized, provided that precautions are taken to adequately clean the membrane of any blood components. However, membrane cleaning by blotting or by use of vacuum devices to remove residue is a difficult procedure, inasmuch as the membrane can be easily damaged.

SUMMARY OF THE INVENTION

In accordance with one embodiment of the present invention, an osmotic sensing head is provided which is relatively simple to maintain and operate in an accurate manner. The sensing head includes walls forming a reference chamber and sample chamber which are connected by a passageway, the passageway being blocked by an osmotic membrane that permits the passage of molecules of a saline solution while stopping the passage of blood protein molecules. The walls of the sample chamber form a pair of tubes, so that a saline storage solution can be removed from the chamber while a blood sample can be introduced therein, by flowing the blood sample into one tube and allowing the saline solution to flow out of the other tube. The sample chamber is of a small volume much less than one milliliter, and therefore is of a volume much less than a blood sample taken in a typical syringe, so that enough blood from the sample is available to completely flush the sample chamber to thereby remove substantially all of the saline storage solution. One of the tubes through which fluid is introduced into the sample chamber, extends at a low angle towards the membrane, so that fluid entering the chamber tends to sweep away any residue lying on the membrane. In order to stretch the membrane a small but controlled amount, it is held between an O-ring and a convex surface which forms a wall of the reference chamber, the convex surface being part of a cone to provide a controlled stretching of the membrane.

The novel features of the invention are set forth with particularity in the appended claims. The invention will be best understood from the following description when read in conjunction with the accompanying drawings.

BRIEF DESCRIPTION OF THE DRAWINGS

FIG. 1 is a perspective view of a sensing head assembly constructed in accordance with the present invention; and FIG. 2 is a view taken on the line 2-2 of FIG. 1.

DESCRIPTION OF THE PREFERRED EMBODIMENTS

As illustrated in FIG. 1, the testing of a blood sample contained in a syringe 10 is performed by a testing apparatus 12 which includes a sensing head 14, a transducer assembly 16 which supports the head, and a pressure indicator 18 which indicates the pressure measured by the transducer assembly. FIG. 2 illustrates details of the sensing head 14 which is designed to receive a blood sample to generate an osmotic pressure characteristic of the particular blood sample, the pressure being detected by a transducer 20 of the transducer apparatus. The head includes an outer member 22 which forms much of the walls of a sample chamber 24, and an inner member 26 which forms most of the walls of a reference chamber 28. The two sensing head parts 22, 26 are normally assembled with an osmotic membrane 30 between the two chambers 24, 28 to permit only small atomic weight molecules to pass between the chambers, as will be more fully discussed below. An O-ring 32 which is held in a groove 34 of the outer member 22 presses the membrane 30 against a convex wall 36 of the inner member, to hold the membrane in a slightly stretched condition to enable its proper operation. The two parts 22, 26 of the head are threaded to permit them to be fastened together with communicating regions 38, 40 blocked only by the membrane 30. The outer member 22 forms a pair of passageways or tubes 42, 44 for the passage of fluid into and out of the sample chamber 24 while the sensing head remains assembled. The inner ends 42i, 44i lead into the sample chamber 24, while the outer ends 42o, 44o lie within nipples 46, 48 designed to attach to resilient plastic tubes 50, 52. The tube 50 leads through a shut-off valve 54 (FIG. 1) to the syringe 10, while the other tube 52 leads through another shut-off valve 56 and to a container for holding fluid prior to disposal of it.

The sensing head 14 is normally stored with a saline solution in both chambers 24, 28, to prevent drying out of the membrane 30. When a sample of whole blood or blood plasma is to be tested, a blood supply such as the syringe 10 is connected to one tube 50 while the other tube 52 is connected to a container, and the two valves 54, 56 are opened. Then blood in the syringe 10 is pumped through the flexible tube 50 and passage 42 into the reference chamber, while the saline storage fluid is allowed to flow out of the chamber through the passage 44 and flexible tube 52. A volume of the sample fluid several times greater than the volume of the sample chamber 24 is pumped into the chamber, to more completely remove saline solution from the chamber. After this process has been completed, one of the valves 54 or 56 is closed to hold in the fluid.

With the blood sample contained in the sample chamber 24 and an isotonic saline solution contained in the reference chamber 28, a pressure imbalance will be created. This is due to the fact that salt molecules of the saline solution in the reference chamber 28 and of the portion of the blood sample which is composed of saline solution, can readily pass through the osmotic membrane 30 and balance out. This is because the membrane is constructed to that it passes only molecules below a certain size such as those of 30,000 atomic weight. Molecules larger than 30,000 atomic weight, which includes the protein molecules present in whole blood and blood plasma, are of a larger molecular weight and cannot pass through the membrane. As a result, saline solution in the reference chamber 28 passes through the membrane into the sample chamber 24 and thereby reduces the hydrostatic pressure in the reference chamber. The transducer 20 measures the hydrostatic pressure of fluid in the chamber 28, and the measured pressure is indicated by the pressure indicator 18 which is coupled to the transducer 20. Inasmuch as the magnitude of the pressure reduction is due to the concentration of protein molecules in the blood sample which is contained in the sample chamber 24, the pressure is a direct indication of the concentration of blood protein molecules in the blood sample. Thus, a determination of the concentration of blood protein molecules can be obtained in a rapid and relatively simple manner.

After the blood sample has been tested, the blood sample should be removed from the sample chamber 24 and replaced by a storage fluid which may be the same as that in the reference chamber 28. This can be accomplished by replacing the syringe 10 with another syringe that is filled with saline solution, opening the valve 54, and pumping in the storage solution while allowing the blood sample and some of the pumped-in storage solution to pass out of the chamber and into a sink or storage container.

One of the problems which arises in utilization of a sensing head is the cleaning of the membrane, particularly of blood platelets or other residue that may tend to settle on the membrane. In accordance with the present invention, at least one of the sample passages 42 has an inner end 42i directed towards the membrane 30 at the area through which saline molecules pass in moving from one chamber to the other, with the passage inner end 42i being oriented at an angle A from an imaginary line normal to the membrane surface, and with the angle A being more than 30°. This results in fluid flowing into the sample chamber tending to wash away any residue on the membrane. The inner ends 42i, 44i of both passages that carry sample fluid, are preferably located on opposite sides of the sample chamber 24 and oriented at an angle of more than 30° from a line normal to the membrane. This results in new fluid entering the sample chamber tending to force the old fluid out of the chamber, and also permits the sensing head to be utilized by passing in either the blood or fluid sample through either of the passages 42 or 44.

The ease of introducing a blood sample by merely pumping in the sample through one passage and allowing storage fluid to flow out through the other passage, is greatly enhanced by utilizing a blood sample of a volume considerably greater than the volume of the sample chamber 24, to permit substantially complete flushing away of any sample fluid in the chamber. In order to permit typical blood samples of perhaps one milliliter to be utilized, the sample chamber is preferably constructed with a volume of less than one-tenth the available blood volume, and therefore preferably has a volume of less than 0.1 milliliter. As a result, the blood sample is more than sufficient to fill the volume of the sample chamber 24 and of the passages 42, 44 leading to and from the sample chamber to wash out the storage fluid.

The osmotic membrane 30 should be held in a slightly stretched condition, but without excessive stretching. The membranes have only a limited lifetime, and therefore must be occasionally replaced by a technician. In order to assure stretching of the membrane, but to only a small extent, the sensing head is constructed so that the membrane is held between the O-ring 32 and the convex wall 36. The convex wall 36 is formed as a portion of a cone, with the angle B between the conical surface and a plane normal to the axis of the cone being on the order of 7°. It has been found that this construction results in slight stretching of the membrane by the O-ring pressing thereagainst, when the inner and outer sensing head members 22, 26 are screwed firmly into one another. After the sensing head has been assembled, it can be readily assembled onto the transducer assembly 16 by inserting the pressure transducer 20, which is sealed by an O-ring 60 to the inner member, and by screwing in a threaded portion of the inner member into a receptacle on the transducer assembly.

A sensing apparatus utilizing a sensing head of the type described above, has been constructed with a sample chamber 24 of 0.1 milliliter volume, and has been utilized with a transducer 20 of model P 23Db manufactured by the Statham Instrument Company. It has been found that this sensing head was simple to operate and provided accurate measurements.

Thus, the invention provides a sensing head which facilitates the introduction of a sample of blood, blood plasma, or other fluid, by utilizing a pair of passages so that the sample can be introduced through one passage while storage fluid can be removed through the other passage. Removal of the storage fluid is enhanced by locating the inner ends of the passages on opposite sides of the sample chamber and orienting them so they are partially directed towards one another. This orientation of at least one passageway, and orienting it so it directs incoming fluid towards the membrane and especially towards the central portion of the membrane, helps to sweep away any residue on the membrane. The introduction of a sample while sweeping away storage fluid in the previously described manner, can be employed with relatively small bood samples, by constructing the sample chamber 24 so that it is of a very small volume compared to a typical blood sample. Installation of the osmotic membrane so that it is tensioned to a small extent, which is kept relatively uniform even for variations of tightening of sensing head parts, is enhanced by utilizing a substantially conical surface on one side of the membrane and an O-ring on the other side, with the conical face tapered at a low angle such as 7°.

Although particular embodiments of the invention have been described and illustrated herein, it is recognized that modifications and variations may readily occur to those skilled in the art and consequently it is intended that the claims be interpreted to cover such modifications and equivalents.

What is claimed is:

1. An osmotic sensing head comprising:

first walls forming a sample chamber for holding a sample fluid;

second walls forming a reference chamber for holding a reference fluid, said reference chamber including a passage with a narrow first end which opens toward said sample chamber and with a second end, said narrow first end being narrower than the area of the sample chamber;

an osmotic membrane disposed over said narrow first end of said reference chamber passage; and pressure measuring means coupled to said second end of said reference chamber passage;

the narrow first end of said reference chamber passage forming a region in contact with said membrane which is narrower than the region of said sample chamber which is in contact with said membrane; and the walls forming said reference chamber including a pair of conduits for carrying fluid to and from said sample chamber, at least a first of said conduits having an end angled to direct fluid entering said reference chamber against the portion of said membrane which lies directly over said narrow first end of said reference chamber passage, whereby to flush away debris lying on the portion of the membrane which lies over the narrow end of the reference chamber.

2. The head described in claim 1 wherein: said narrow first end of reference chamber passage lies under the center of said membrane, and said first conduit end is directed at the center of said membrane.

3. A method for determining the amount of protein molecules in a sample of blood-like material, comprising:

establishing a reference saline solution in a reference chamber that has a narrow end open to a first side of a membrane which permits the movement of saline solution molecules but does not permit the movement of at least some blood protein molecules therethrough, and establishing a storage solution in a sample chamber that is open to a second side of said membrane;

changing the fluid on said second side of said membrane by withdrawing said storage solution from said second side of said membrane and flowing a sample fluid containing blood plasma onto said second side of said membrane;

measuring the pressure of fluid in said reference chamber; and again changing the fluid on said second side of said membrane by withdrawing said sample fluid from said second side of said membrane and flowing a storage solution onto said second side of said membrane;

said step of again changing the fluid including directing a stream of said storage solution into said sample chamber directly against the membrane portion which lies over the narrow end of the reference chamber, while flowing said sample fluid out of said sample chamber.

* * * * *